(12) United States Patent
Zhou

(10) Patent No.: US 10,098,834 B2
(45) Date of Patent: *Oct. 16, 2018

(54) EXTENDED RELEASE OF NEUREGULIN FOR TREATING HEART FAILURE

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/892,183

(22) PCT Filed: May 22, 2014

(86) PCT No.: PCT/CN2014/078154
§ 371 (c)(1),
(2) Date: Nov. 18, 2015

(87) PCT Pub. No.: WO2014/187342
PCT Pub. Date: Nov. 27, 2014

(65) Prior Publication Data
US 2016/0089329 A1   Mar. 31, 2016

Related U.S. Application Data

(60) Provisional application No. 61/826,433, filed on May 22, 2013.

(51) Int. Cl.
*A61K 38/16* (2006.01)
*A61K 38/18* (2006.01)
*C07K 14/475* (2006.01)
*A61K 9/00* (2006.01)

(52) U.S. Cl.
CPC ........ *A61K 9/0019* (2013.01); *A61K 38/1883* (2013.01)

(58) Field of Classification Search
None
See application file for complete search history.

(56) References Cited

U.S. PATENT DOCUMENTS

| | | |
|---|---|---|
| 5,530,109 A | 6/1996 | Goodearl et al. |
| 5,686,102 A | 11/1997 | Gross et al. |
| 5,716,930 A | 2/1998 | Goodearl et al. |
| 5,736,154 A | 4/1998 | Fuisz |
| 5,741,511 A | 4/1998 | Lee et al. |
| 5,834,229 A | 11/1998 | Vandlen et al. |
| 5,886,039 A | 3/1999 | Kock et al. |
| 5,941,868 A | 8/1999 | Kaplan et al. |
| 6,197,801 B1 | 3/2001 | Lin |
| 6,258,374 B1 | 7/2001 | Friess et al. |
| 6,589,229 B1 | 7/2003 | Connelly et al. |
| 7,226,907 B1 | 6/2007 | Zhou |
| 7,612,164 B2 | 11/2009 | Zhou |
| 7,686,787 B2 | 3/2010 | Moberg et al. |
| 7,795,212 B2 | 9/2010 | Zhou |
| 7,964,555 B2 | 6/2011 | Zhou |
| 8,476,405 B2 | 7/2013 | Zhou |
| 8,609,620 B2 | 12/2013 | Zhou |
| 8,785,387 B2 | 7/2014 | Zhou |
| 9,012,400 B2 | 4/2015 | Zhou |
| 9,089,524 B2 | 7/2015 | Zhou |
| 9,340,597 B2 | 5/2016 | Zhou |
| 9,434,777 B2 | 9/2016 | Zhou |
| 9,555,076 B2 | 1/2017 | Zhou |
| 9,580,515 B2 | 2/2017 | Zhou |
| 9,655,949 B2 | 5/2017 | Zhou |
| 2005/0065760 A1 | 3/2005 | Murtfeldt et al. |
| 2005/0277887 A1* | 12/2005 | Douglas ............ A61M 5/14248 604/173 |
| 2006/0199767 A1 | 9/2006 | Zhou |
| 2007/0129296 A1 | 6/2007 | Zhou |
| 2007/0190127 A1 | 8/2007 | Zhou |
| 2007/0213264 A1 | 9/2007 | Zhou |
| 2009/0156488 A1 | 6/2009 | Zhou |
| 2011/0135595 A1 | 6/2011 | Zhou |
| 2011/0229444 A1 | 9/2011 | Zhou |
| 2013/0078235 A1 | 3/2013 | Zhou |
| 2014/0364366 A1 | 12/2014 | Zhou |
| 2015/0284440 A1 | 10/2015 | Zhou |
| 2016/0089329 A1 | 3/2016 | Zhou |

(Continued)

FOREIGN PATENT DOCUMENTS

| | | |
|---|---|---|
| CN | 101310779 A | 11/2008 |
| CN | 101394861 A | 3/2009 |

(Continued)

OTHER PUBLICATIONS

Carraway et al., "Neuregulin-2, a new ligand of ErbB/ErbB4-receptor tyrosine kinase," *Nature*, 387:512-516 (1997).
Chang et al., "Ligands for ErbB-family receptors encoded by a neuregulin-like gene," *Nature*, 387:509-512 (1997).
Corfas et al., "Neuregulin 1-erbB signaling and the molecular/cellular basis of schizophrenia," *Nature Neuroscience*, 7(6):575-580 (2004).
Higashiyama et al., "A novel brain-derived member of the epidermal growth factor family that interacts with ErbB3 and ErbB4," *J. Biochem.*, 122:675-680 (1997).
Hijazi et al., "NRG-3 in human breast cancers: activation of multiple erbB family proteins," *Int. J. Oncol.*, 13:1061-1067 (1998).
Holmes et al., "Identification of heregulin, a specific activator of p185$^{erbB2}$," *Science*, 256:1205-1210 (1992).

(Continued)

*Primary Examiner* — Christine J Saoud
*Assistant Examiner* — Jon M Lockard
(74) *Attorney, Agent, or Firm* — Jones Day

(57) ABSTRACT

The present invention provides methods and kits for preventing, treating or delaying various cardiovascular diseases or disorders especially heart failure by extended release of neuregulin to a mammal. Moreover, the extended release of neuregulin is administered by subcutaneous infusion with a pump.

63 Claims, 6 Drawing Sheets
Specification includes a Sequence Listing.

(56) References Cited

U.S. PATENT DOCUMENTS

| | | |
|---|---|---|
| 2016/0095903 A1 | 4/2016 | Zhou |
| 2016/0297859 A1 | 10/2016 | Zhou |
| 2017/0007671 A1 | 1/2017 | Zhou |
| 2017/0189489 A1 | 7/2017 | Zhou |
| 2017/0232068 A1 | 8/2017 | Zhou |

FOREIGN PATENT DOCUMENTS

| | | |
|---|---|---|
| WO | WO 97/09425 A1 | 3/1997 |
| WO | WO 00/37095 A1 | 6/2000 |
| WO | WO 00/64400 A2 | 11/2000 |
| WO | WO 00/78347 A1 | 12/2000 |
| WO | WO 01/70307 A1 | 9/2001 |
| WO | WO 02/48191 A2 | 6/2002 |
| WO | WO 03/099300 A1 | 12/2003 |
| WO | WO 2003/099320 A1 | 12/2003 |
| WO | WO 2003/099321 A1 | 12/2003 |
| WO | WO 04/030716 A2 | 4/2004 |
| WO | WO 04/030717 A2 | 4/2004 |
| WO | WO 2007/062594 A1 | 6/2007 |
| WO | WO 2007/076701 A1 | 7/2007 |
| WO | WO 2008/028405 A1 | 3/2008 |
| WO | WO 2009/033373 A1 | 3/2009 |
| WO | WO 2010/060265 A1 | 6/2010 |
| WO | WO 2010/060266 A1 | 6/2010 |
| WO | WO 2010/142141 A1 | 12/2010 |
| WO | WO 2011/091723 A1 | 8/2011 |
| WO | WO 2013/053201 A1 | 4/2013 |
| WO | WO 2014/187342 A1 | 11/2014 |
| WO | WO 2015/101182 A1 | 7/2015 |
| WO | WO 2016/045493 A1 | 3/2016 |
| WO | WO 2016/058493 A1 | 4/2016 |

OTHER PUBLICATIONS

Sadick et al., "Analysis of heregulin-induced ErbB2 phosphorylation with a high-throughput kinase receptor activation enzyme-linked immunosorbant assay," *Anal. Biochem.*, 235:207-214 (1996).

Watson et al., *Molecular Biology of the Gene*, 4$^{th}$ Edition, The Bejacmin/Cummings Publishing Company, Inc., Menlo Park, CA, p. 224 (1987).

Hervent et al., "Left ventricular diastolic dysfunction in obese diabetic mice is attenuated by pharmacological inhibition of dipeptidyl peptidase IV," Eur. J. Heart Failure Supplements, 12:S12-S16, Abstract 388, (2013).

* cited by examiner

EXTENDED RELEASE OF NEUREGULIN FOR TREATING HEART FAILURE

This application is a U.S. national stage application of PCT/CN2014/078154, having an international filing date of May 22, 2014, which claims the benefit of priority of U.S. Provisional application Ser. No. 61/826,433 filed May 22, 2013, each of which the entire contents are incorporated herein by reference.

The instant application contains a Sequence Listing which has been submitted electronically in ASCII format and is hereby incorporated by reference in its entirety. Said ASCII copy, created on May 20, 2014, is named 11748-039-228_SL.txt and is 3,198 bytes in size.

FIELD OF THE INVENTION

The invention relates generally to compositions and methods for preventing, treating or delaying various cardiovascular diseases or disorders especially heart failure by extended release of neuregulin. In particular, this invention relates to the administration of neuregulin to a mammal via subcutaneous infusion with a pump.

BACKGROUND OF THE INVENTION

Heart failure affects approximately five million Americans, and more than 550,000 new patients are diagnosed with the condition each year. Current drug therapy for heart failure is primarily directed to angiotensin-converting enzyme (ACE) inhibitors, which are vasodilators that cause blood vessels to expand, lowering blood pressure and reducing the heart's workload. While the percent reduction in mortality has been significant, the actual reduction in mortality with ACE inhibitors has averaged only 3%-4%, and there are several potential side effects. Additional limitations are associated with other options for preventing or treating heart failure. For example, heart transplantation is clearly more expensive and invasive than drug treatment, and it is further limited by the availability of donor hearts. Uses of mechanical devices, such as biventricular pacemakers, are similarly invasive and expensive. Thus, there has been a need for new therapies given the deficiencies in current therapies.

One promising new therapy involves administration of neuregulin (hereinafter referred to as "NRG") to a patient suffering from or at risk of developing heart failure. NRGs, a family of EGF-like growth factors, comprises a family of structurally related growth and differentiation factors that include NRG1, NRG2, NRG3 and NRG4 and isoforms thereof, are involved in an array of biological responses: stimulation of breast cancer cell differentiation and secretion of milk proteins; induction of neural crest cell differentiation to Schwann cells; stimulation of skeletal muscle cell synthesis of acetylcholine receptors; and, promotion of myocardial cell survival and DNA synthesis. In vivo studies of neuregulin gene-targeted homozygous mouse embryos with severe defects in ventricular trabeculae formation and dorsal root ganglia development indicate that neuregulin is essential for heart and neural development.

NRGs bind to the EGF receptor family, which comprises EGFR, ErbB2, ErbB3 and ErbB4, each of which plays an important role in multiple cellular functions, including cell growth, differentiation and survival. They are protein tyrosine kinase receptors, consisting of an extracellular ligand-binding domain, transmembrane kinase domain and cytoplasmic tyrosine kinase domain. After NRG binds to the extracellular domain of ErbB3 or ErbB4, it induces a conformational change that leads to heterodimer formation between ErbB3, ErbB4 and ErbB2 or homodimer formation between ErbB4 itself, which results in phosphorylation of the receptor's C-terminal domain inside the cell membrane. The phosphorylated intracellular domain then binds additional signal proteins inside the cell, activating the corresponding downstream AKT or ERK signaling pathway, and inducing a series of cell reactions, such as stimulation or depression of cell proliferation, cell differentiation, cell apoptosis, cell migration or cell adhesion. Among these receptors, mainly ErbB2 and ErbB4 are expressed in the heart.

It has been shown that the EGF-like domains of NRG-1, ranging in size from 50 to 64-amino acids, are sufficient to bind to and activate these receptors. Previous studies have shown that neuregulin-1β (NRG-1β) can bind directly to ErbB3 and ErbB4 with high affinity. The orphan receptor, ErbB2, can form heterodimer with ErbB3 and ErbB4 with higher affinity than ErbB3 or ErbB4 homodimers. Research in neural development has indicated that the formation of the sympathetic nervous system requires an intact NRG-1β, ErbB2 and ErbB3 signaling system. Targeted disruption of the NRG-1β or ErbB2 or ErbB4 led to embryonic lethality due to cardiac development defects. Recent studies also highlighted the roles of NRG-1β, ErbB2 and ErbB4 in the cardiovascular development as well as in the maintenance of adult normal heart function. NRG-1β has been shown to enhance sarcomere organization in adult cardiomyocytes. Extended release of NRG via intravenous infusion significantly improves or protects against deterioration in myocardial performance in distinct animal models of heart failure as well as in clinical trials. These results make NRG-1 promising as a lead compound for the treatment of heart failure. While the administration of NRG to the patients via intravenous infusion for consecutive days at hospital is to some extent inconvenient and expensive, there is a need to develop an effective and convenient method of using NRG for the prevention, treatment or delaying of cardiovascular diseases, in particular, heart failure.

SUMMARY OF THE INVENTION

It has been discovered by applicant that extended release of neuregulin (NRG) through intravenous infusion greatly improves the effect of NRG in the treatment of heart failure compared to NRG administered by non-extended release methods. Extended release of NRG through intravenous infusion also has the benefit of reducing the adverse side effects of NRG compared to NRG administered by non-extended release methods. This invention further provides compositions and methods for preventing, treating or delaying various cardiovascular diseases or disorders especially heart failure by extended release of NRG through subcutaneous infusion to a mammal, particularly in humans. In particular, this invention relates to compositions and methods for preventing, treating or delaying various cardiovascular diseases or disorders, especially heart failure, by extended release of NRG using a portable mini pump for subcutaneous infusion.

It has been discovered by applicant that NRG enhances cardiac muscle cell differentiation and organization of sarcomeric and cytoskeleton structure, as well as cell adhesion. It has been also discovered by applicant that NRG through intravenous infusion significantly improves or protects against deterioration in myocardial performance in distinct animal models of heart failure and in clinical trials. Neuregulin, neuregulin polypeptide, neuregulin derivatives, or compounds which mimic the activities of neuregulins, fall within the scope of the present invention.

Thus, in a first aspect of the present invention, a method is provided for preventing, treating or delaying various cardiovascular diseases or disorders, especially heart failure, comprising providing extended release of neuregulin into a mammal in need thereof. In one embodiment of the method, the extended release of neuregulin into a mammal enhances the EF values of the left ventricle of mammal. In another embodiment of the method, the extended release of neuregulin into a mammal reduces Left Ventricular End-Diastolic Volume (LVEDV) or Left Ventricular End-Systolic Volume (LVESV). In another embodiment of the method, the extended release of neuregulin into a mammal improves six minute walk distance and quality of life. In another embodiment of the method, the extended release of neuregulin into a mammal reduces side effects. In some embodiment of the method for preventing, treating or delaying cardiovascular diseases or disorders in a mammal, the extended release of neuregulin into a mammal comprises the use of a mini pump. In some embodiment of the method, the extended release of neuregulin into a mammal is administered by subcutaneous infusion.

In a second aspect, an extended release composition or formulation of neuregulin is provided for preventing, treating or delaying various cardiovascular diseases or disorders, especially heart failure. In one embodiment, using the compositions or formulations of neuregulin enhances the EF values of the left ventricle of a mammal. In another embodiment, using the compositions or formulations of neuregulin reduces Left Ventricular End-Diastolic Volume (LVEDV) or Left Ventricular End-Systolic Volume (LVESV). In another embodiment, using the compositions or formulations of neuregulin improves of six minute walk distance and quality of life. In another embodiment, using the compositions or formulations of neuregulin reduces side effects. In some embodiments, the extended release composition or formulation of neuregulin is administered by subcutaneous infusion with a pump, for example, a syringe pump. In some embodiments, the syringe pump is a mini pump. In further embodiments, the mini pump is an insulin pump.

In a third aspect, an effective dose and/or an effective dose range of extended release neuregulin is provided for preventing, treating or delaying various cardiovascular diseases or disorders especially heart failure. In some embodiments, the neuregulin is administered by subcutaneous infusion. In some embodiments, the effective dose of neuregulin is 0.3 μg/kg. In some embodiments, the effective dose of neuregulin is 1.2 μg/kg. In some embodiments, the effective dose of neuregulin is 2.0 μg/kg. In some embodiments, the effective dose of neuregulin is 3.0 μg/kg. In some embodiments, an effective dose range of neuregulin is 0.3-3.0 μg/kg. In some embodiments, an effective dose range of neuregulin is 1.2-2.0 μg/kg.

In a forth aspect, the present invention provides a kit comprising a neuregulin composition or formulation and a portable mini pump. In some embodiments, the kit further comprises an instruction for using the kit for preventing, treating or delaying heart failure in a mammal. In some embodiments, the portable mini pump is an insulin pump.

DETAILED DESCRIPTION OF THE INVENTION

A. Definitions

Figure 1:
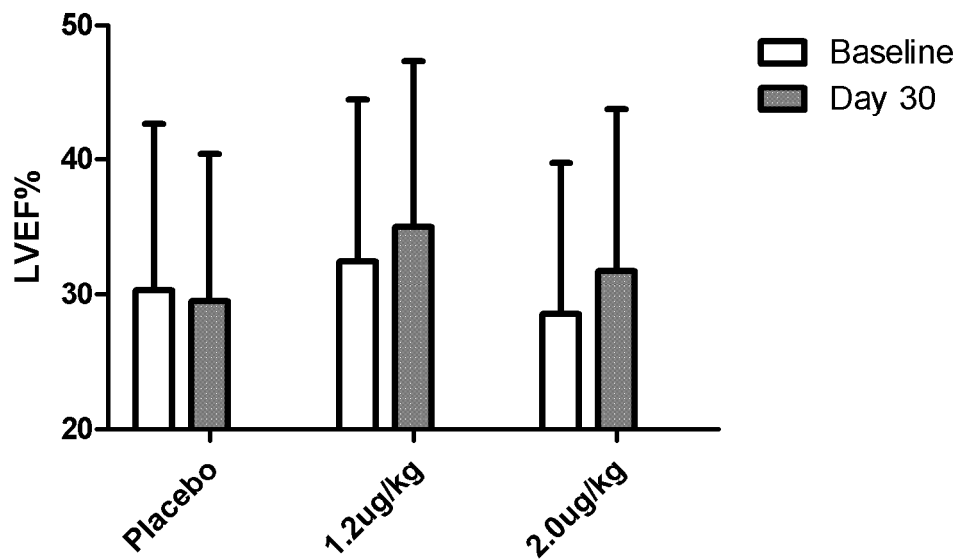
FIG. 1: Results of LVEF % at baseline and day 30.

For clarity of disclosure, and not by way of limitation, the detailed description of the invention hereinafter is divided into the subsections that follow. All publications mentioned herein are incorporated by reference to disclose and describe the methods and/or materials in connection with which the publications are cited.

Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

As used herein, "neuregulin" or "NRG" used in the present invention refers to proteins or peptides that can bind and activate ErbB2, ErbB3, ErbB4 or combinations thereof, including but not limited to all neuregulin isoforms, neuregulin EGF-like domain alone, polypeptides comprising neuregulin EGF-like domain, neuregulin mutants or derivatives, and any kind of neuregulin-like gene products that also activate the above receptors as described in detail below. Neuregulin also includes NRG-1, NRG-2, NRG-3 and NRG-4 proteins, peptides, fragments and compounds that mimic the activities of neuregulin. Neuregulin used in the present invention can activate the above ErbB receptors and modulate their biological reactions, e.g., stimulate acetylcholine receptor synthesis in skeletal muscle cell; and/or improve cardiocyte differentiation, survival and DNA synthesis. Neuregulin also includes those variants with conservative amino acid substitutions that do not substantially alter their biological activity. Suitable conservative substitutions of amino acids are known to those of skill in the art and may be made generally without altering the biological activity of the resulting molecule. Those of skill in the art recognize that, in general, single amino acid substitutions in non-essential regions of a polypeptide do not substantially alter biological activity (see, e.g., Watson et al., *Molecular Biol-*

*ogy of the Gene*, 4<sup>th</sup> Edition, 1987, The Bejacmin/Cummings Pub. co., p. 224). In preferred embodiments, neuregulin used in the present invention binds to and activates ErbB2/ErbB4 or ErbB2/ErbB3 heterodimers, for example, but not for the purpose of restriction, peptides including the 177-237 residues of NRG-1 β2 isoform containing the amino acid sequence: SHLVKCAEKEKTFCVNGGECF MVKDL-SNPSRYLCKCPNEFTGDRCQNYVMASFYKAEELYQ (SEQ ID NO:1). The peptides including the 177-237 residues of NRG-1 β2 isoform comprise the EGF-like domain, which has been proved to be sufficient to bind to and activate the receptors.

As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., *Science*, 256: 1205-1210 (1992); U.S. Pat. Nos. 5,530,109 and 5,716,930; Hijazi et al., *Int. J. Oncol.*, 13:1061-1067 (1998); Chang et al., *Nature*, 387:509-512 (1997); Carraway et al., *Nature*, 387:512-516 (1997); Higashiyama et al., *J. Biochem.*, 122: 675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1 (amino acid residues 177-226 SHLVK-CAEKEKTFCVNGGECFMVKDLSNPSRYLCKCPNEFT-GDRCQNYVM (SEQ ID NO:2); amino acid residues 177-240 SHLVKCAEKEKTFCVNGGECFMVKDLSNPSRYLC KCPNEFTGDRCQNYVMASFY KAEELYQKRV (SEQ ID NO:3)), each of which is considered to be an exemplary neuregulin of the invention. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro (SEQ ID NO:4), as described in U.S. Pat. No. 5,834,229.

The neuregulin protein, can be formulated for oral, topical, inhalational, buccal (e.g., sublingual), parenteral (e.g., subcutaneous, intramuscular, intradermal, or intravenous), transdermal administration or any other suitable route of administration. The most suitable route in any given case will depend on the nature and severity of the condition being treated and on the nature of the particular neuregulin protein, which is being used. The neuregulin protein can be administered alone. Alternatively and preferably, the neuregulin protein is co-administered with a pharmaceutically acceptable carrier or excipient. Any suitable pharmaceutically acceptable carrier or excipient can be used in the present method (See e.g., *Remington: The Science and Practice of Pharmacy*, Alfonso R. Gennaro, ed., Mack Publishing Company, April 1997; and *Remington's Pharmaceutical Sciences*, 18th ed., Gennaro, ed., Mack Publishing Co. (1990)).

As used herein, a "pump" is a drug delivery device that employs subcutaneous infusions of therapeutic fluids, drugs, proteins, and/or other compounds and has the property of continuous precise dosing of the medication in their supply. A pump can employ a subcutaneous catheter for continuous subcutaneous infusion. The catheter can be external or the catheter port can be embedded into the pump mechanism. A mini pump is a device which can export fluids accurately and it is portable and handy. As an example, an insulin pump is a medical device used for the administration of insulin or other agents in the treatment of diabetes mellitus or other diseases, also known as continuous subcutaneous insulin infusion therapy. An insulin pump can be configured to be attached to a disposable thin plastic tube or a catheter through which insulin or other drug substance passes into the tissue. The catheter can be inserted subcutaneously and changed as needed. A pump can be configured in external devices, which connect to a patient, and can be configured in implantable devices, which are implanted inside of the body of a patient. External pumps can include devices designed for use in a stationary location, such as a hospital, a clinic, or the like, and further can include devices configured for ambulatory or portable use, such as pumps designed to be carried by a patient, or the like. External pumps contain reservoirs of fluidic media, such as, but not limited to, fluidic media containing neuregulin protein.

External pumps can be connected in fluid flow communication to a patient, for example, through suitable hollow tubing. The hollow tubing can be connected to a hollow needle that is designed to pierce the skin of the patient and to deliver fluidic media there through. Alternatively, the hollow tubing can be connected directly to the patient as through a cannula, or the like. An external pump can be worn or otherwise attached on or underneath clothing of the patient. Examples of suitable pumps include, but are not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump (Medtronic; Northridge, Calif.), and any similar devices known by those skilled in the art.

Examples of external pump type delivery devices are described in U.S. patent application Ser. No. 11/211,095, filed Aug. 23, 2005, published as US2006/0264894 and issued as U.S. Pat. No. 7,686,787, titled "Infusion Device And Method With Disposable Portion," and Published PCT Application WO 01/70307 (PCT/US01/09139) titled "Exchangeable Electronic Cards For Infusion Devices," Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

Pharmaceutically acceptable compositions and methods for their administration that may be employed for use in this invention include, but are not limited to, those described in U.S. Pat. Nos. 5,736,154; 6,197,801; 5,741,511; 5,886,039; 5,941,868; 6,258,374; and 5,686,102.

It should be noted that a person skilled in the art such as an attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

In practical use, the neuregulin protein, alone or in combination with other agents, may be combined as the active ingredient in intimate admixture with a pharmaceutical carrier or excipient, such as beta-cyclodextrin and/or 2-hydroxy-propyl-beta-cyclodextrin, according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, including but not limited to water, glycols, oils, buffers, sugar, preservatives, liposomes, stabilizing agents, and the like known to those of skill in the art. Examples of such parenteral compositions include, but are not limited to dextrose 5% w/v, normal saline or other solutions. Exemplary buffers include, but are not limited to, acetate, citrate and phosphate. Exemplary stabilizing agents include, but are not limited to, proteins such as albumin, for example, human serum albumin, gelatin, and the like. Exemplary sugars include, but are not limited to, glucose (dextrose), sucrose, fructose, mannitol, sorbitol, and the like. Exemplary salts include, but are not limited to, potassium bicarbonate, sodium bicarbonate, potassium chloride, sodium chloride and the like. Exemplary components of a pharmaceutical composition are described, for example, in Remington, supra, 1997, and Remington's, supra, 1990. The total dose of the neuregulin protein, alone or in combination with other agents to be administered, may be administered in a vial of intravenous fluid, ranging from about 1 ml to 2000 ml.

In another embodiment, a kit of the invention further comprises a needle or syringe, preferably packaged in sterile form, for injecting the composition, and/or a packaged alcohol pad. Instructions are optionally included for administration of the composition by a physician or by the patient.

As used herein, "protein" is synonymous with "polypeptide" or "peptide" unless the context clearly dictates otherwise.

As used herein, "activity unit" or "EU" or "U" means the quantity of standard product that can induce 50% maximal reaction. In other words, to determine the activity unit for a given active agent, the EC50 must be measured. For example, if the EC50 for a batch of product was 0.1 µg, then that would be one unit. Further, if 1 µg of that product is being used, then 10 EU (1/0.1) is being used. The EC50 can be determined by any method known in the art suitable for making such a determination, including the method employed by the inventors as disclosed herein. This determination of the activity unit is important for quality control of genetically engineered products and clinically used drugs, and permits product from different pharmaceuticals and/or different batch numbers to be quantified with uniform criteria.

The following is an exemplary, rapid, sensitive, high flux and quantitative method for determination of biological activity of NRG-1 through combining NRG with cell surface ErbB3/ErbB4 molecule and indirect mediation of ErbB2 phosphorylation (See e.g., Michael D. Sadick et al., 1996, *Analytical Biochemistry*, 235:207-214 and WO03/099300).

Briefly, the assay, termed a kinase receptor activation enzyme-linked immunosorbant assay (KIRA-ELISA), consists of two separate microtiter plates, one for cell culture, ligand stimulation, and cell lysis/receptor solubilization and the other plate for receptor capture and phosphotyrosine ELISA. The assay was developed for analysis of NRG-induced ErbB2 activation and utilizes the stimulation of intact receptor on the adherent breast carcinoma cell line, MCF-7. Membrane proteins are solubilized via Triton X-100 lysis and the receptor is captured in ELISA wells coated with ErbB2-specific antibodies with no cross-reaction to ErbB3 or ErbB4. The degree of receptor phosphorylation is then quantified by antiphosphotyrosine ELISA. A reproducible standard curve is generated with an EC50 of approximately 360 pM for heregulin beta 1 (177-244) (amino acid residues 177-244 SHLVKCAEKEKTFCVNGGECFMVKDL-SNPSRYLC KCPNEFTGDRCQNYVMASFY KAEELY-QKRVLTIT (SEQ ID NO:5)). When identical samples of HRG beta 1 (177-244) are analyzed by both the KIRA-ELISA and quantitative antiphosphotyrosine Western Blot analysis, the results correlate very closely with one another. The assay described in this report is able to specifically quantify tyrosine phosphorylation of ErbB2 that results from the interaction of HRG with ErbB3 and/or ErbB4.

Since most of the genetically engineered medicines are proteins and polypeptides, their activity can be determined by their amino acid sequences or the activity center formed by their spatial structure. Activity titer of protein and polypeptide is not consistent with their absolute quality, therefore cannot be determined with weight unit as that of chemical drugs. However, biological activity of genetically engineered medicines is generally consistent with their pharmacodynamics, and a titer determination system established through a given biological activity can determine its titer unit. Therefore, biological activity determination can be part of a process of titering the substance with biological activity and is an important component of quality control of genetically engineered product. It is important to determine biological activity criteria for quality control of genetically engineered product and clinically used drugs.

Quantity of standard product that can induce 50% maximal reaction is defined as an activity unit (1 EU). Accordingly, product from different pharmaceuticals and of different batch numbers can be quantified with uniform criteria.

As used herein, an "effective dose" of an active agent for preventing, treating or delaying a particular disease is a dose that is sufficient to ameliorate, or in some manner reduce the symptoms associated with the disease. The dose may cure the disease but, typically, is administered in order to ameliorate the symptoms of the disease.

In particular embodiments, an effective dose of neuregulin can be at least 0.2 µg/kg/day, 0.3 µg/kg/day, 0.4 µg/kg/day, 0.5 µg/kg/day, 0.6 µg/kg/day, 0.7 µg/kg/day, 0.8 µg/kg/day, 0.9 µg/kgday, 1.0 µg/kg/day, 1.1 µg/kg/day, 1.2 µg/kg/day, 1.3 µg/kg/day, 1.4 µg/kg/day, 1.5 µg/kg/day, 1.6 µg/kg/day, 1.7 µm/kg/day, 1.8 µg/kg/day, 1.9 µg/kg/day, 2.0 µg/kg/day, 2.1 µg/kg/day, 2.2 µg/kg/day, 2.3 µg/kg/day, 2.4 µg/kg/day, 2.5 µg/kg/day, 2.6 µg/kg/day, 2.7 µg/kg/day, 2.8 µg/kg/day, 2.9 µg/kg/day, or 3.0 µg/kg/day. In one embodiment, an effective dose of neuregulin is 1.2 µg/kg/day. In another embodiment, an effective dose of neuregulin is 2.0 µg/kg/day. In one embodiment, an effective dose of neuregulin is 3.0 µg/kg. In one embodiment, an effective dose range of neuregulin is 0.3-3.0 µg/kg/day. In one embodiment, an effective dose range of neuregulin is 1.2-2.0 µg/kg/day.

As used herein, "active agent" means any substance intended for the diagnosis, cure, mitigation, treatment, or prevention of disease in humans and other animals, or to otherwise enhance physical and mental well-being.

As used herein, "amelioration" of the symptoms of a particular disorder by administration of a particular active agent refers to any lessening, whether permanent or temporary, lasting or transient, that can be attributed to or associated with administration of the agent.

As used herein, "treat", "treatment" and "treating" refer to any manner in which the symptoms of a condition, disorder or disease are ameliorated or otherwise beneficially altered. The effect may be prophylactic in terms of completely or partially preventing a disease or symptom thereof, and/or the effect may be therapeutic in terms of a partial or complete reduction of a sign or symptom associated with a disease, cure for a disease and/or reducing an adverse effect attributable to the disease. Treatment also encompasses any pharmaceutical use of the compositions herein.

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, viral, toxic or idiopathic forms. Chronic cardiac hypertrophy is a significantly diseased state which is a precursor to congestive heart failure and cardiac arrest.

As used herein, "ejection fraction" or "EF" means the portion of blood that is pumped out of a filled ventricle as the result of a heartbeat. It may be defined by the following formula: (LV diastolic volume–LV systolic volume)/LV diastolic volume.

The present invention provide methods and compositions for extended release of neuregulin for preventing, treating or delaying various cardiovascular diseases or disorders, such as heart failure. Extended release of neuregulin allows for simplification of administration scheme, improves clinical efficacy and attenuates adverse events, e.g., related to high blood level of neuregulin. It is contemplated that extended release of neuregulin over a certain period of time could induce or maintain expression of certain genes for cardiomyocyte growth and/or differentiation, remodeling of muscle cell sarcomeric and cytoskeleton structures, or cell-cell adhesions.

Extended release of neuregulin provides a continuous therapeutic level of neuregulin over a period of time. In some embodiments, neuregulin is released over a period of 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or longer. In some embodiments, neuregulin is released over a period of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or longer. In another embodiment, neuregulin is released over a period of 1 week, 2 weeks, 3 weeks, 4 weeks or longer. The administration can optionally occur for consecutive hours or on consecutive days or weeks, if desired. In another embodiment, neuregulin is released over a period of 1 month, 2 months, 3 months, 4 months, 5 months, 6 months, 7 months, 8 months, 9 months, 10 months, 11 months, 12 months or longer. In another embodiment, neuregulin is released over a period of 1 year, 2 years, 3 years, 4 years, 5 years, or longer. In some embodiments, neuregulin is released over a period of between 1 hour and 2 weeks, between 2 hours and 2 weeks, between 4 hours to 24 hours, between 4 days and 10 days.

The amount of time over which neuregulin is released may depend on various factors such as the extended release technology or technologies used.

Neuregulin can also be administered in a dosing schedule or "therapeutic cycle". Daily dosage of neuregulin in the therapeutic cycle is described in detail below. The therapeutic cycle can last 2 days, 5 days, 7 days, 10 days, two weeks, 1 month, 3 month, 6 month, 1 year or longer. In general, the recommended daily dose range of neuregulin per kilogram of body weight of the patients in the methods of the invention for the conditions described herein lie within the range of from about 0.001 µg to about 1000 mg per day. Specially, a total daily dose range per kilogram of body weight of the patients should be between 0.001 µg per day and 15 mg per day, 0.005 µg per day and 10 mg per day, 0.01 µg per day and 5 mg per day, 0.1 µg per day and 1 mg per day, 0.5 µg per day and 100 µg per day, 1 µg per day and 10 µg per day, 1.2 µg per day and 2.4 µg per day, 1.2 µg per day and 2.2 µg per day, or 1.2 µg per day and 2.0 µg per day. In managing the patient, the therapy can be initiated at a lower dose, perhaps about 0.1 µg to about 0.3 µg, and increased if necessary up to about 1 µg to 1000 µg per day as either a single dose or divided doses, depending on the patient's global response. It may be necessary to use dosages of the active ingredient outside the ranges disclosed herein in some cases, as will be apparent to those of ordinary skill in the art.

In certain embodiments, neuregulin is administered daily for each day of the therapeutic cycle. In certain embodiments, neuregulin is administered consecutively for 3 days, 4 days, 5 days, 6 days, 7 days, 8 days, 9 days, 10 days, 2 weeks, 1 month, 3 months, 6 months, 1 year or longer. In certain embodiments, neuregulin is administered to the patients for an induction regimen. In some optimized embodiments, the induction regimen includes an administration of neuregulin for at least 3, 5, 7, 10 or 15 consecutive days. In some optimized embodiments, the induction regimen includes administration of neuregulin at least 2, 4, 6, 8, 10, 12, 16, 20, 24 consecutive hours every day. In some optimized embodiments, neuregulin is administered to the patients for a maintenance regimen for at least 3 months, 6 months, 12 months, 1 year, 5 years or even longer after the induction regimen. It is understood that other time periods disclosed herein can be used for an induction or maintenance regimen.

In one embodiment, the invention provides a method for preventing, treating or delaying a cardiovascular disease or disorder in a mammal, the method comprising subcutaneous extended release of neuregulin into a mammal in an amount of 0.3 µg/kg/day to 3.0 µg/kg/day, wherein the subcutaneous extended release of neuregulin into a mammal is accomplished through the use of a pump. The extended release of neuregulin can be provided by administering neuregulin in an extended release formulation, such as a suitable formulation for administering by use of a pump. In another embodiment, the invention provides a method for preventing, treating or delaying a cardiovascular disease or disorder in a mammal, the method comprising administering subcutaneously an extended release of neuregulin into a mammal in an amount of 0.3 µg/kg/day to 3.0 µg/kg/day, wherein the subcutaneous extended release of neuregulin into a mammal is accomplished through the use of a pump.

In a particular embodiment of a method of the invention, the disease or disorder being treated with neuregulin is heart failure, for example, in a mammal such as a human. In another embodiment, the subcutaneous extended release of neuregulin into a mammal is accomplished through the use of a syringe pump. The syringe pump can be, for example, a mini pump such an insulin pump.

In another embodiment of a method of the invention, the neuregulin can in an amount of 1.2 µg/kg/day to 2.0 µg/kg/day, or other amounts disclosed herein. In a particular embodiment, the neuregulin is in an amount of 1.2 µg/kg/day. In another particular embodiment, the neuregulin is in an amount of 2.0 µg/kg/day. In another particular embodiment, the neuregulin is in an amount of 6 EU/kg/day to 60 EU/kg/day. In another embodiment, the neuregulin is in an amount of 24 EU/kg/day to 40 EU/kg/day. In another embodiment, the neuregulin is in an amount of 24 EU/kg/day. In another embodiment, the neuregulin is in an amount of 40 EU/kg/day.

In still another embodiment of a method of the invention, the neuregulin can be administered to the mammal for an induction regimen. In one embodiment, the induction regimen includes an administration of neuregulin for at least 3, 5, 7, 10 or 15 consecutive days. It is understood that other number of days of administration can be used, if desired, as disclosed herein. In another embodiment, the neuregulin can be administered for at least 2, 4, 6, 8, 10, 12, 16, 20, 24 consecutive hours every day. It is understood that other number of hours of administration can be used, if desired, as disclosed herein.

In another embodiment, the neuregulin is administered to the patients for a maintenance regimen after the induction regimen. In one embodiment, the maintenance regimen can include an administration of neuregulin for at least 3 months, 6 months, 12 months, 5 years or even longer after the induction regimen. In another embodiment, the maintenance regimen includes a repeat of the induction regimen every 3 months, 6 months or 12 months.

In still another embodiment, the extended release of neuregulin into a mammal enhances the ejection fraction (EF) value of the mammal. The ejection fraction (EF) represents the volumetric fraction of blood pumped out of the left and right ventricle with each heartbeat or cardiac cycle. Methods of measuring the ejection fraction are well known to those skilled in the art.

In yet another embodiment, the extended release of neuregulin into a mammal reduces the Left Ventricular End-Diastolic Volume (LVEDV) of the mammal. As is well known in the art, the end-diastolic volume (EDV) is the volume of blood in the right and/or left ventricle at end load or filling in (diastole). In another embodiment, the extended release of neuregulin into a mammal reduces the Left Ventricular End-Systolic Volume (LVESV) of the mammal. As is well known in the art, end-systolic volume (ESV) is the volume of blood in a ventricle at the end of contraction, or systole, and the beginning of filling, or diastole. Methods of measuring the LVEDV and/or LVESV are well known to those skilled in the art.

In still another embodiment of a method of the invention, the extended release of neuregulin into a mammal improves 6 Minute Walk Distance (6 MWD) of the mammal. In yet another embodiment, the extended release of neuregulin into a mammal improves quality of life of the mammal. The effectiveness of neuregulin at improving measurements of heart disease and/or improved patient outcomes are described herein in the Examples.

The invention additional provides a kit for preventing, treating or delaying a cardiovascular disease or disorder in a mammal, the kit comprising a neuregulin composition or formulation and a pump. The kit can be used, for example, to treat a patient having a disease or disorder that is heart failure. The patient can be a mammal such as a human. In an embodiment of the kit, the pump can be a syringe pump. In a particular embodiment, the pump can be a mini pump. In another particular embodiment, the pump can be an insulin pump The characteristics of a patient having a disease or disorder such as heart disease or heart failure are well known to those skilled in the art (see, for example, Cecil Textbook of Medicine, 20th ed., Bennett and Plum, eds., W.B. Saunders Company, Philadelphia (1996); Harrison's Principles of Internal Medicine, 14th ed., Fauci et al., eds., McGraw-Hill, San Francisco (1998). One skilled in the art such as a physician can readily determine a patient having a disease or disorder suitable for treatment with the methods of the invention providing sustained release of neuregulin.

It is well known in the art that a patient's heart failure can be classified according to the severity of their symptoms. The most commonly used classification system is the New York Heart Association (NYHA) Functional Classification. It places patients in one of four categories based on how much they are limited during physical activity, as follows: Class I: patients with cardiac disease but resulting in no limitation of physical activity. Ordinary physical activity does not cause undue fatigue, palpitation, dyspnea or anginal pain; Class II: patients with cardiac disease resulting in slight limitation of physical activity. They are comfortable at rest. Ordinary physical activity results in fatigue, palpitation, dyspnea or anginal pain; Class III: patients with cardiac disease resulting in marked limitation of physical activity. They are comfortable at rest. Less than ordinary activity causes fatigue, palpitation, dyspnea or anginal pain; Class IV: patients with cardiac disease resulting in inability to carry on any physical activity without discomfort. Symptoms of heart failure or the anginal syndrome may be present even at rest. If any physical activity is undertaken, discomfort increases. In some embodiments, all of the NYHA classified patients (Class I-Class IV) are suitable for the methods of the invention. In some preferred embodiments, the NYHA classified Class II and/or Class III patients are suitable for the methods of the invention.

In certain embodiments, in a therapeutic cycle neuregulin is administered on day 1 of the cycle and the cycle concludes with one or more days of no neuregulin administration. In some embodiments, neuregulin is administered daily for 3, 5, 7, 10 or 15 days followed by a resting period in a therapeutic cycle.

It is understood that modifications which do not substantially affect the activity of the various embodiments of this invention are also provided within the definition of the invention provided herein. Accordingly, the following examples are intended to illustrate but not limit the present invention.

EXAMPLES

Example 1

A Randomized, Parallel, Double-blinded, Multi-center, Placebo Controlled Study to Evaluate the Efficacy and Safety of Recombinant Human Neuregulin 1 in Subjects with Stable Chronic Heart Failure 1. Introduction: To evaluate the efficacy and safety of recombinant human neuregulin-1 for subcutaneous infusion on chronic heart failure, a phase II, randomized, parallel, double-blinded, placebo controlled study was carried out in multiple clinical centers in the USA. A total of 67 patients with NYHA Class II or III stable chronic heart failure were enrolled. Subjects underwent interrogation of their implantable cardioverter-defibrillator (ICD) between 1 and 7 days before randomization to drug. Subjects were randomized into one of three treatment arms at the end of screening, following baseline cardiac computed tomography (CT). The study consisted of five periods, a Screening and Baseline period (Study Days −21 to Day −3), a treatment period (Study Days 1 through 10, with a daily infusion start time of 8 am±2 hours), discharge (Day 11), a follow-up period (Study Days 30, 90 and 180±5 days) and a final follow-up visit through Day 365 (±5 days) to last in duration of approximately 12 months. All subjects were instructed to adhere to their current stable cardiac regimen during study participation.

2. Diagnosis and Main Inclusion Criteria

Subjects were considered for enrollment if they had chronic heart failure with a NYHA classification of II or III, and were on a stable regimen of ACEI/angiotensin receptor blocker (ARB), beta-blocker, and/or diuretic for at least 3 months prior to receiving study medication and were anticipated to remain on the stable regimen through the treatment period. Subjects were required to have an ICD implanted at least 3 months prior to receiving study medication and have left ventricular ejection fraction (LVEF) of ≤40% as determined at screening by 2-D echocardiography.

3. Products, Dose, Duration, Mode of Administration, and Batch/Lot Number:

On Day 1 through Day 10, subjects received a subcutaneous infusion of one of the following treatments: placebo (Lot number: TC2952, 250 µg per vial), or Neucardin™ (Lot number: TC2965, 250 µg/5000 EU per vial) doses of 1.2 µm/kg/day (24 EU/kg/day) or 2.0 µm/kg/day (40 EU/kg/day).

Identity of Investigational Product(s): Neucardin™ (Lot number: TC2965) and matching placebo (Lot number: TC2952) were supplied in a clear glass vial containing 250 µg of active drug or placebo per vial. The active drug and matching placebo were white to off-white powders. The study drug was prepared according to the randomization code provided using the subjects' body weight in kilograms to prepare daily doses of 1.2 µg/kg, 2.0 µg/kg, and placebo appearing as a clear, colorless solution, essentially free of visible particulates. The storage temperature was 2-8° C. and the drug was to be protected from light and out of reach of children.

SC infusion pump: Medtronic Paradigm 722 insulin pump. Using the Medtronic pump reservoir extract 1.6 mL of dissolved drug into the reservoir and the flow rate of the pump is 0.2 ml/h for 8 hours.

4. Criteria for Evaluation:

Efficacy: Efficacy assessments included cardiac CT at baseline and Day 30; NYHA Classification, 6-minute walk test, Quality of Life Questionnaire (Kansas City Cardiomyopathy Questionnaire), and NT-proBNP levels at screening and baseline, and Days 30, 90, 180 and 365; and 2-D echocardiography at screening and baseline, Day 30, and Day 90.

Safety: Safety assessments included monitoring of adverse events (AEs), adverse reactions (ADRs), serious adverse events (SAEs), vital signs, physical exam, pulse oximetry, ecg parameters (e.g. QTc, QRS, HR, PR, RR, T-wave flattening/inversion, ST-elevation), anti-Neucardin™ antibody levels, pericardial fluid as measured by cardiac CT (mL, mild, moderate, large), ICD interrogation (inappropriate firing, yes or no), 2D echocardiography pericardial fluid (mL, mild, moderate, large) and laboratory parameters (chemistry, hematology, and urology). In cardiology, the QTc refers to QT interval, which is a measure of the time between the start of the Q wave and the end of the T wave in the heart's electrical cycle. The QT interval represents electrical depolarization and repolarization of the ventricles. A lengthened QT interval is a marker for the potential of ventricular tachyarrhythmias like torsades de pointes and a risk factor for sudden death. The Q, R, and S waves occur in rapid succession, do not all appear in all leads, and reflect a single event, and thus are usually considered together. A Q wave is any downward deflection after the P wave. An R wave follows as an upward deflection, and the S wave is any downward deflection after the R wave. The T wave follows the S wave, and in some cases an additional U wave follows the T wave. Heart Rate (HR) is the speed of the heartbeat, specifically the number of heartbeats per unit of time. The PR interval is also commonly termed the PQ interval, when a Q wave is measured by ECG. The RR is the interval between successive Rs during ECG. The RR interval variations present during resting conditions represent beat-by-beat variations in cardiac autonomic inputs. CT refers to X-ray computed tomography. ICD refers to implantable cardioverter defibrillator.

5. Results. The Results are Described Below.

5.1 LVEF

TABLE 1

Results of LVEF % and LVEF % absolute change at baseline and day 30.

|  | Placebo (N = 19) | 1.2 µg/kg/day (N = 22) | 2.0 µg/kg/day (N = 19) |
| --- | --- | --- | --- |
| Baseline | 30.29 | 32.46 | 28.54 |
| Day 30 | 29.47 | 34.99 | 31.74 |
| Day 30 - Baseline | −0.82 | 2.53 | 3.20 |
| Day 30 - Placebo | — | 3.35 | 4.02 |

Figure 2:
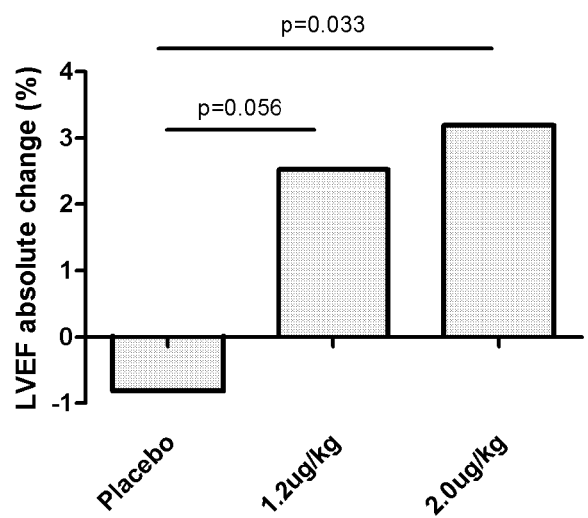
FIG. 2: LVEF % absolute change at day 30 compared to baseline.

The value of LVEF % was decreased in placebo group while the value was increased in both neuregulin groups (See FIG. 1 and Table 1). The mean absolute change was −0.82%, 2.53% and 3.20% respectively in placebo group, 1.2 µg/kg and 2.0 µg/kg group (See FIG. 2 and Table 1), indicating Neucardin™ improved cardiac function by the route of subcutaneous infusion.

5.2 LVEDV

TABLE 2

Results of LVEDV (ml) and LVEDV (ml) absolute change at baseline and day 30.

|  | Placebo (N = 19) | 1.2 µg/kg/day (N = 22) | 2.0 µg/kg/day (N = 19) |
| --- | --- | --- | --- |
| Baseline | 287.49 | 289.43 | 274.50 |
| Day 30 | 297.71 | 281.26 | 276.86 |
| Day 30 - Baseline | 10.22 | −8.16 | 2.36 |
| Day 30 - Placebo | — | −18.38 | −7.86 |

Figure 3:
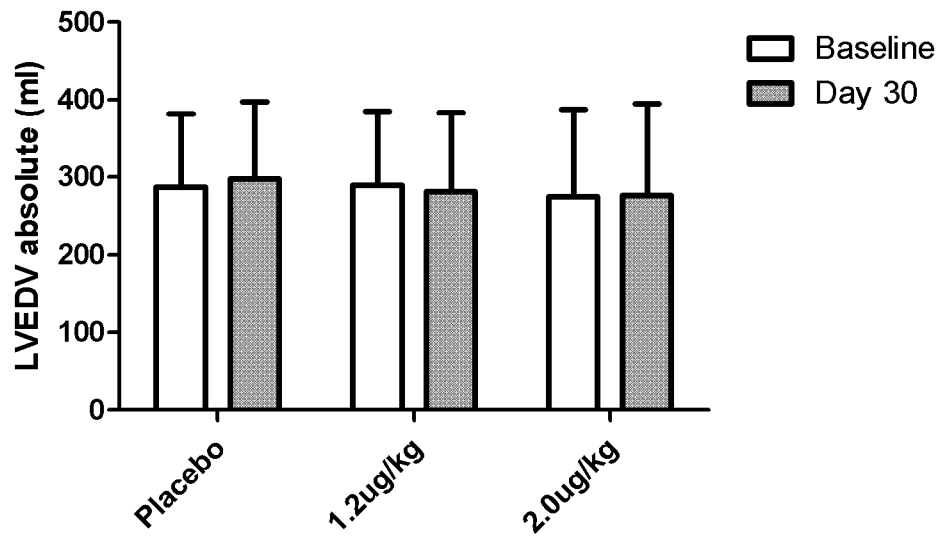
FIG. 3: Results of LVEDV at baseline and day 30.
Figure 4:
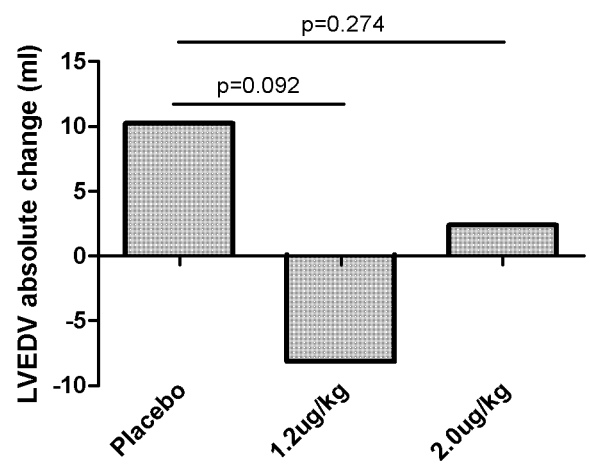
FIG. 4: LVEDV absolute change at day 30 compared to baseline.

The value of LVEDV was increased in placebo group, while in 2.0 µg/kg group, the increase of LVEDV was not as much as that of placebo group, and the value was significantly decreased in 1.2 µg/kg group (See FIG. 3 and Table 2). The mean absolute change was 10.22 ml, −8.16 ml and 2.36 ml, respectively, in placebo group, 1.2 µg/kg and 2.0 µg/kg group (See FIG. 4 and Table 2). Regarding the value of LVEDV, 1.2 µg/kg group was better than 2.0 µg/kg group.

5.3 LVESV

TABLE 3

Results of LVESV (ml) and LVESV (ml) absolute change at baseline and day 30.

|  | Placebo (N = 19) | 1.2 µg/kg/day (N = 22) | 2.0 µg/kg/day (N = 19) |
| --- | --- | --- | --- |
| Baseline | 206.79 | 202.29 | 205.24 |
| Day 30 | 216.12 | 191.71 | 200.06 |
| Day 30 - Baseline | 9.33 | −10.58 | −5.19 |
| Day 30 - Placebo | — | −19.91 | −14.52 |

Figure 5:
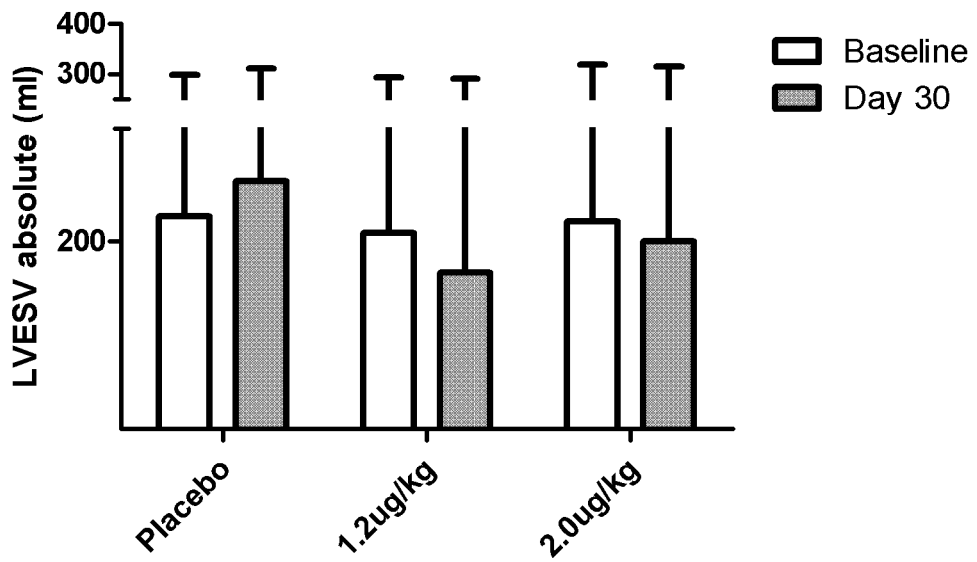
FIG. 5: Results of LVESV at baseline and day 30.
Figure 6:
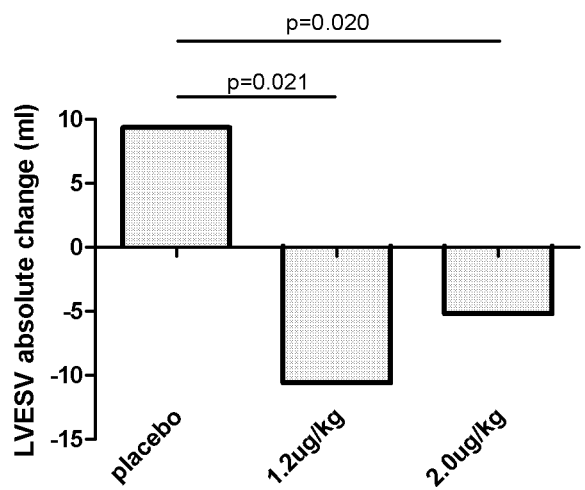
FIG. 6: LVESV absolute change at day 30 compared to baseline.

The value of LVESV was increased in placebo while the value was decreased in both neuregulin groups (See FIG. 5 and Table 3). The mean absolute change was 9.33 ml, −10.58 ml and −5.19 ml respectively in placebo group, 1.2 µg/kg and 2.0 µg/kg group (See in FIG. 6 and table 3). Regarding the value of LVESV, 1.2 µg/kg group was better than 2.0 µg/kg group. Both LVEDV and LVESV data showed that Neucardin™ efficiently reversed ventricular remodeling in CHF patients by the route of subcutaneous infusion.

5.4 Six Minute Walk Test

TABLE 4

Results of increased walk distance (m) & post walk dyspnea & post walk fatigue at Day 30, 90, 180 and 365 compared to baseline.

|  | Time (days) | Placebo (N = 19) | 1.2 ug/kg/day (N = 22) | 2.0 ug/kg/day (N = 19) |
| --- | --- | --- | --- | --- |
| Increased walk distance (m) | 30 | 19.2 | 41.4 | 1.7 |
|  | 90 | 21.6 | 52.2 | −2.0 |
|  | 180 | 30.5 | 47.7 | 11.7 |
|  | 365 | 39.4 | 62.2 | −24.4 |
| Post walk dyspnea (score) | 30 | −0.3 | −0.8 | −0.6 |
|  | 90 | −0.1 | −0.7 | −0.7 |
|  | 180 | −0.8 | −0.8 | −0.3 |
|  | 365 | 0.3 | −0.8 | −0.5 |
| Post walk fatigue (score) | 30 | 0.1 | −1.4 | −1.0 |
|  | 90 | 0.2 | −1.1 | −0.4 |
|  | 180 | −0.2 | −1.3 | 0.2 |
|  | 365 | 0.3 | −1.3 | 0.2 |

Figure 7:
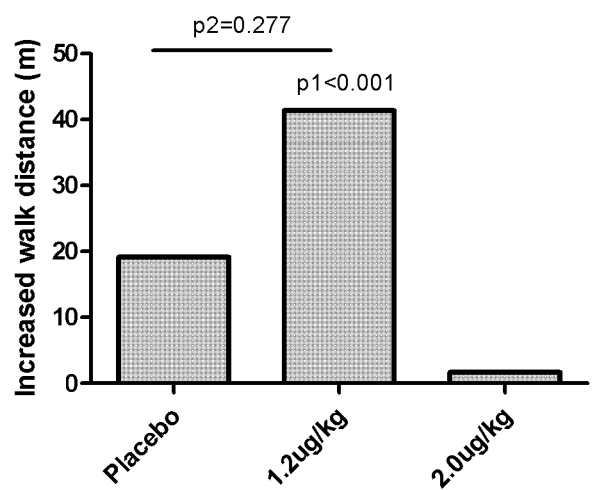
FIG. 7: Results of increased walk distance at day 30 compared to baseline.
Figure 8:
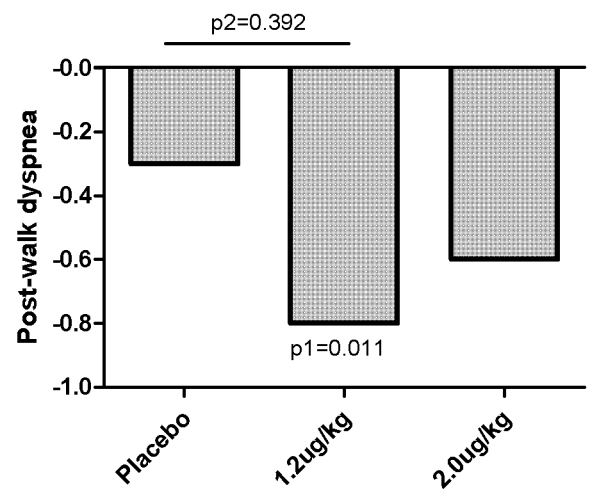
FIG. 8: Results of post walk dyspnea at day 30 compared to baseline.
Figure 9:
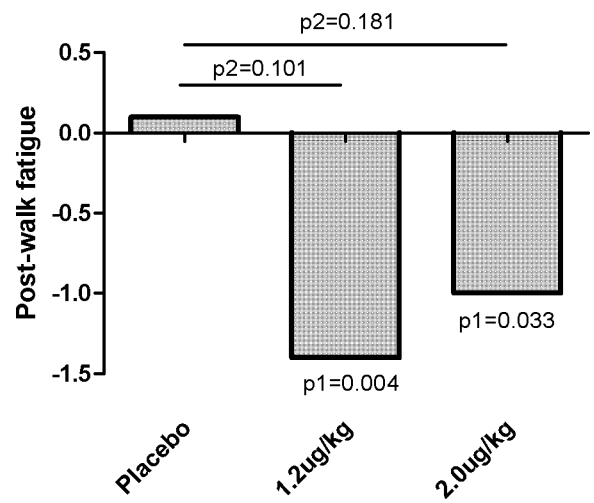
FIG. 9: Results of post walk fatigue at day 30 compared to baseline.

Increased walk distances in 1.2 µg/kg group (41.4 m at day 30, 52.2 m at day 90, 47.7 m at day 180, 62.2 m at day 365) were all longest in the 3 groups and the increased walk distances in placebo group (19.2 m at day 30, 21.6 m at day 90, 30.5 m at day 180, 39.4 m at day 365) was longer than that in 2.0 µg/kg group (1.7 m at day 30, −2.0 m at day 90, 11.7 m at day 180, −24.4 m at day 365) (See FIG. 7 and Table 4). The observed increase in walk distance observed in the 1.2 µg/kg/day group exceeded what would have been predicted based on prior studies that utilized intravenous administration of neuregulin. With regard to the results of post walk dyspnea and fatigue at day 30 and at day 90, both neuregulin groups were better than placebo group (See FIGS. 8 and 9 and Table 4).

5.5 Quality of Life Day 30, 90, 180 and 365

TABLE 5

Quality of Life Analysis.

| Time (days) | Placebo (N = 19) | 1.2 ug/kg/day (N = 22) | 2.0 ug/kg/day (N = 19) |
| --- | --- | --- | --- |
| 30 | 4.825 | 15.873 | 9.649 |
| 90 | 2.778 | 15.079 | 9.649 |
| 180 | 8.333 | 17.460 | 7.353 |
| 365 | 10.000 | 16.228 | 7.870 |

Figure 10:
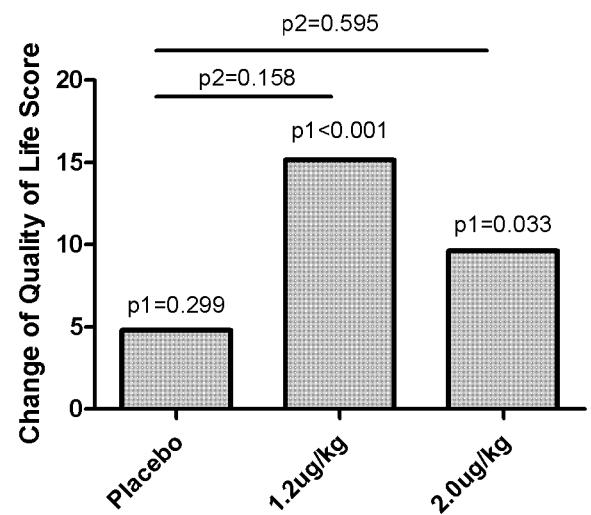
FIG. 10: Change of quality of life score at day 30 compared to baseline.

As seen in FIG. 10, the score of quality of life was increased by 4.825, 15.152 and 9.649 respectively in placebo group, 1.2 µg/kg and 2.0 µg/kg group (see also Table 5). Higher score means better quality of life. As seen in Table 5, the score of quality of life in the 1.2 µg/kg group was highest of the 3 groups. Scores of all 3 groups were increased while the 1.2 µg/kg group increased much more than the placebo group (See FIG. 10). The observed increase in quality of life score observed in the 1.2 µg/kg/day group exceeded what would have been predicted based on prior studies that utilized intravenous administration of neuregulin.

5.6 Results of NT-proBNP Median Value Change at Baseline, Day 30, 90, 180 and 365.

TABLE 6

NT-proBNP median value change (PG/ML).

| Time (days) | Placebo (N = 19) | 1.2 µg/kg/day (N = 22) | 2.0 µg/kg/day (N = 19) |
| --- | --- | --- | --- |
| Baseline | 779.00 | 472.00 | 678.50 |
| Day 30 - Baseline | −14.00 | −73.00 | 45 |
| Day 90 - Baseline | 16.00 | −55.00 | −70.50 |
| Day 180 - Baseline | −24.00 | −69.00 | −50.50 |
| Day 365 - Baseline | 68.00 | −83.50 | −20.00 |

NT-proBNP is widely used as a diagnostic or prognostic marker for heart failure because it's typically higher in patients with worse outcome. As seen in Table 6, the level of NT-proBNP in 1.2 µg/kg group was lowest in the 3 groups and 1.2 µg/kg group was decreased much more than the placebo group.

5.7 NYHA Classification Day 30

TABLE 7

Percentage of NYHA classification at baseline and day 30.

|  |  | NYHA I | NYHA II | NYHA III | NYHA IV |
| --- | --- | --- | --- | --- | --- |
| Baseline | Placebo | 0 | 84.2% | 15.8% | 0 |
|  | 1.2 ug/kg/day | 0 | 81.8% | 18.2% | 0 |
|  | 2.0 ug/kg/day | 0 | 73.7% | 26.3% | 0 |
| Day 30 | Placebo | 5.3% | 84.2% | 10.5% | 0 |
|  | 1.2 ug/kg/day | 13.6% | 72.7% | 13.6% | 0 |
|  | 2.0 ug/kg/day | 15.8% | 57.9% | 26.3% | 0 |

TABLE 8

Numbers and percentage of patients changed by 1 degree or more in NYHA classification compare to baseline.

| Change compare to baseline | placebo | 1.2 µg/kg/day | 2.0 µg/kg/day |
| --- | --- | --- | --- |
| Decrease by 1° or more | 2 (9.5%) | 5 (20.8%) | 6 (27.3%) |
| No change | 19 (90.5%) | 17 (70.8%) | 13 (59.1%) |
| Increased by 1° or more | 0 | 1 (4.2%) | 3 (13.6%) |

Figure 11:
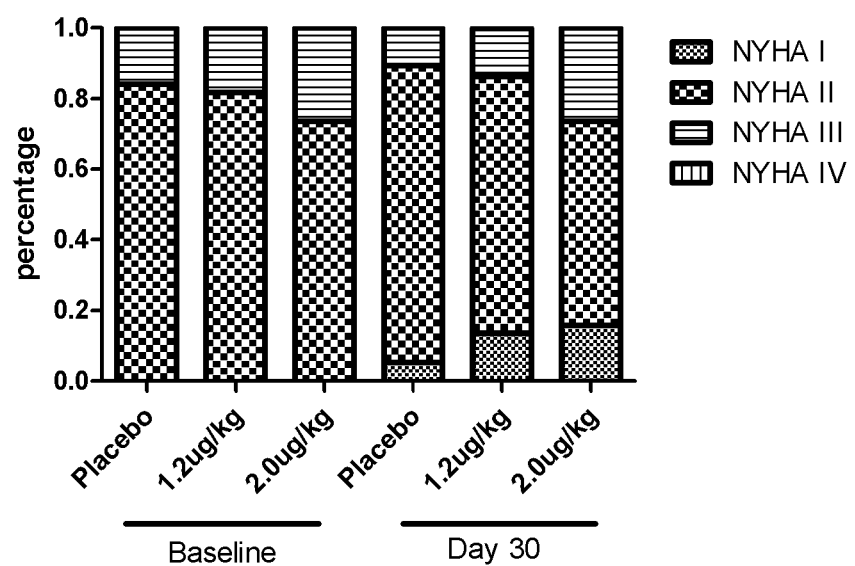
FIG. 11: Percentage of NYHA classification at baseline and day 30.

As seen in FIG. 11 and Tables 7 and 8, more patients decreased by 1 or more degree in NYHA classification with Neucardin™ treatment. The observed decrease in NYHA classification exceeded what would have been predicted based on prior studies that utilized intravenous administration of neuregulin.

5.8 Safety Evaluation

TABLE 9

Overall summary of adverse events (AE).

|  | 1.2 µg/kg/day (N = 24) | 2.0 µg/kg/day (N = 22) | Placebo (N = 21) | Total (N = 67) |
|---|---|---|---|---|
| Number (%) of Subjects with AEs | 21 (87.5) | 21 (95.5) | 15 (71.4) | 57 (85.1) |
| Number (%) of Subjects with AEs by Maximum Relatedness to Study Drug | | | | |
| Unrelated[1] | 6 (25.0) | 5 (22.7) | 9 (42.9) | 20 (29.9) |
| Not Unrelated | 15 (62.5) | 16 (72.7) | 6 (28.6) | 37 (55.2) |

TABLE 9-continued

Overall summary of adverse events (AE).

|  | 1.2 µg/kg/day (N = 24) | 2.0 µg/kg/day (N = 22) | Placebo (N = 21) | Total (N = 67) |
|---|---|---|---|---|
| Number (%) of Subjects with AEs by Maximum Severity | | | | |
| Mild | 16 (66.7) | 10 (45.5) | 9 (42.9) | 35 (52.2) |
| Moderate | 4 (16.7) | 6 (27.3) | 3 (14.3) | 13 (19.4) |
| Severe | 1 (4.2) | 5 (22.7) | 3 (14.3) | 9 (13.4) |
| Number (%) of Subjects with Serious AEs | 1 (4.2) | 6 (27.3) | 4 (19.0) | 11 (16.4) |

As seen in Table 9, safety data showed that Neucardin™ administration increased the incidence of adverse events, while most of these were mild to moderate, especially in 1.2 µg/kg group. In the 1.2 µg/kg group, the incidence of serious adverse events was decreased, suggesting Neucardin™ treatment improved the overall situation of CHF patients.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for treating heart failure in a mammal, the method comprising administering subcutaneous extended release of neuregulin into a mammal in an amount of 0.3 µg/kg/day to 3.0 µg/kg/day, wherein the subcutaneous extended release of neuregulin into a mammal is accomplished through the use of a pump.

2. The method of claim 1, wherein the mammal is human.

3. The method of claim 1, wherein the subcutaneous extended release of neuregulin into a mammal is accomplished through the use of a syringe pump.

4. The method of claim 3, wherein the syringe pump is a mini pump.

5. The method of claim 4, wherein the mini pump is an insulin pump.

6. The method of claim 1, wherein neuregulin is in an amount of 1.2 µg/kg/day to 2.0 µg/kg/day.

7. The method of claim 1, wherein neuregulin is in an amount of 1.2 µg/kg/day.

8. The method of claim 1, wherein neuregulin is in an amount of 2.0 µg/kg/day.

9. The method of claim 1, wherein neuregulin is in an amount of 6 EU/kg/day to 60 EU/kg/day.

10. The method of claim 1, wherein neuregulin is in an amount of 24 EU/kg/day to 40 EU/kg/day.

11. The method of claim 1, wherein neuregulin is in an amount of 24 EU/kg/day.

12. The method of claim 1, wherein neuregulin is in an amount of 40 EU/kg/day.

13. The method of claim 1, wherein the neuregulin is administered to the mammal for an introduction regimen.

14. The method of claim 13, wherein the introduction regimen includes an administration of neuregulin for at least 3, 5, 7, 10 or 15 consecutive days.

15. The method of claim 14, wherein the introduction regimen includes an administration of neuregulin for at least 3 consecutive days.

16. The method of claim 14, wherein the introduction regimen includes an administration of neuregulin for at least 5 consecutive days.

17. The method of claim 14, wherein the introduction regimen includes an administration of neuregulin for at least 7 consecutive days.

18. The method of claim 14, wherein the introduction regimen includes an administration of neuregulin for at least 10 consecutive days.

19. The method of claim 14, wherein the introduction regimen includes an administration of neuregulin for at least 15 consecutive days.

20. The method of claim 13, wherein the introduction regimen includes an administration of neuregulin for 10 consecutive days.

21. The method of claim 13, wherein the neuregulin is administered for at least 2, 4, 6, 8, 10, 12, 16, 20 or 24 consecutive hours every day.

22. The method of claim 21, wherein the neuregulin is administered for at least 2 consecutive hours every day.

23. The method of claim 21, wherein the neuregulin is administered for at least 4 consecutive hours every day.

24. The method of claim 21, wherein the neuregulin is administered for at least 6 consecutive hours every day.

25. The method of claim 21, wherein the neuregulin is administered for at least 10 consecutive hours every day.

26. The method of claim 21, wherein the neuregulin is administered for at least 12 consecutive hours every day.

27. The method of claim 21, wherein the neuregulin is administered for at least 16 consecutive hours every day.

28. The method of claim 21, wherein the neuregulin is administered for at least 20 consecutive hours every day.

29. The method of claim 21, wherein the neuregulin is administered for at least 24 consecutive hours every day.

30. The method of claim 13, wherein the neuregulin is administered for 8 consecutive hours every day.

31. The method of claim 13, wherein the neuregulin is administered to the patients for a maintenance regimen after the introduction regimen.

32. The method of claim 31, wherein the maintenance regimen includes an administration of neuregulin for at least 3 months, 6 months, 12 months, 1 year, 5 years or even longer after the introduction regimen.

33. The method of claim 32, wherein the maintenance regimen includes administration of neuregulin for at least 3 months.

34. The method of claim 32, wherein the maintenance regimen includes administration of neuregulin for at least 6 months.

35. The method of claim 32, wherein the maintenance regimen includes administration of neuregulin for at least 12 months.

36. The method of claim 32, wherein the maintenance regimen includes administration of neuregulin for at least 1 year.

37. The method of claim 32, wherein the maintenance regimen includes administration of neuregulin for at least 5 years.

38. The method of claim 32, wherein the maintenance regimen includes administration of neuregulin for longer than 5 years.

39. The method of claim 31, wherein the maintenance regimen includes a repeat of the induction regimen every 3 months, 6 months or 12 months.

40. The method of claim 39, wherein the maintenance regimen includes a repeat of the induction regimen every 3 months.

41. The method of claim 39, wherein the maintenance regimen includes a repeat of the induction regimen every 6 months.

42. The method of claim 39, wherein the maintenance regimen includes a repeat of the induction regimen every 12 months.

43. The method of claim 1, wherein the extended release of neuregulin into the mammal enhances the ejection fraction (EF) value of the mammal.

44. The method of claim 1, wherein the extended release of neuregulin into the mammal reduces the Left Ventricular End-Diastolic Volume (LVEDV) of the mammal.

45. The method of claim 1, wherein the extended release of neuregulin into the mammal reduces the Left Ventricular End-Systolic Volume (LVESV) of the mammal.

46. The method of claim 1, wherein the extended release of neuregulin into the mammal improves 6 Minute Walk Distance (6 MWD) of the mammal.

47. The method of claim 1, wherein the extended release of neuregulin into the mammal improves quality of life of the mammal.

48. The method of claim 1, wherein the neuregulin comprises the EGF-like domain of NRG-1, NRG-2, NRG-3 or NRG-4.

49. The method of claim 48, wherein the neuregulin comprises the EGF-like domain of NRG-1.

50. The method of claim 48, wherein the neuregulin comprises the EGF-like domain of NRG-2.

51. The method of claim 48, wherein the neuregulin comprises the EGF-like domain of NRG-3.

52. The method of claim 48, wherein the neuregulin comprises the EGF-like domain of NRG-4.

53. The method of claim 1, wherein the neuregulin comprises an amino acid sequence selected from the group consisting of SEQ ID NO:1, SEQ ID NO:2, SEQ ID NO:3 and SEQ ID NO:4.

54. The method of claim 53, wherein the neuregulin comprises the amino acid sequence SEQ ID NO:1.

55. The method of claim 53, wherein the neuregulin comprises the amino acid sequence SEQ ID NO:2.

56. The method of claim 53, wherein the neuregulin comprises the amino acid sequence SEQ ID NO:3.

57. The method of claim 53, wherein the neuregulin comprises the amino acid sequence SEQ ID NO:4.

58. The method of claim 1, wherein the neuregulin is selected from the group consisting of NRG-1, NRG-2, NRG-3 and NRG-4.

59. The method of claim 58, wherein the neuregulin is NRG-1.

60. The method of claim 58, wherein the neuregulin is NRG-2.

61. The method of claim 58, wherein the neuregulin is NRG-3.

62. The method of claim 58, wherein the neuregulin is NRG-4.

63. The method of claim 1, wherein the neuregulin is NRG-1 β2.

* * * * *

SEQUENCE LISTING

```
<160> NUMBER OF SEQ ID NOS: 5

<210> SEQ ID NO 1
<211> LENGTH: 61
<212> TYPE: PRT
<213> ORGANISM: Unknown
<220> FEATURE:
<223> OTHER INFORMATION: Description of Unknown: Unknown neuregulin
      sequence

<400> SEQUENCE: 1

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 2
<211> LENGTH: 50
<212> TYPE: PRT
<213> ORGANISM: Unknown
<220> FEATURE:
<223> OTHER INFORMATION: Description of Unknown: Unknown neuregulin
      sequence

<400> SEQUENCE: 2

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30
```

```
Leu Cys Lys Cys Pro Asn Glu Phe Thr Gly Asp Arg Cys Gln Asn Tyr
        35                  40                  45

Val Met
    50

<210> SEQ ID NO 3
<211> LENGTH: 64
<212> TYPE: PRT
<213> ORGANISM: Unknown
<220> FEATURE:
<223> OTHER INFORMATION: Description of Unknown: Unknown neuregulin
      sequence

<400> SEQUENCE: 3

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln Lys Arg Val
    50                  55                  60

<210> SEQ ID NO 4
<211> LENGTH: 23
<212> TYPE: PRT
<213> ORGANISM: Unknown
<220> FEATURE:
<223> OTHER INFORMATION: Description of Unknown: Unknown neuregulin
      sequence

<400> SEQUENCE: 4

Ala Glu Lys Glu Lys Thr Phe Cys Val Asn Gly Gly Glu Cys Phe Met
1               5                   10                  15

Val Lys Asp Leu Ser Asn Pro
            20

<210> SEQ ID NO 5
<211> LENGTH: 68
<212> TYPE: PRT
<213> ORGANISM: Unknown
<220> FEATURE:
<223> OTHER INFORMATION: Description of Unknown: Unknown neuregulin
      sequence

<400> SEQUENCE: 5

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln Lys Arg Val
    50                  55                  60

Leu Thr Ile Thr
65
```